United States Patent [19]

Crossley

[11] 4,191,761
[45] Mar. 4, 1980

[54] COPPER COMPLEXES OF TETRAHYDROQUINOLINE DERIVATIVES HAVING ANTI-ULCER ACTIVITY

[75] Inventor: Roger Crossley, Reading, England

[73] Assignee: John Wyeth & Brother Ltd., Taplow, England

[21] Appl. No.: 858,482

[22] Filed: Dec. 8, 1977

[30] Foreign Application Priority Data

Dec. 18, 1976 [GB] United Kingdom .............. 52962/76

[51] Int. Cl.$^2$ .................... C07D 215/48; A61K 31/47
[52] U.S. Cl. ........................................ 424/245; 546/6; 546/10; 546/169; 546/93; 546/79; 546/104
[58] Field of Search ................... 260/270 K; 424/245; 546/10, 6

[56] References Cited

U.S. PATENT DOCUMENTS 4,009,169  2/1977  Curran et al. .................... 424/258

FOREIGN PATENT DOCUMENTS 1284394  8/1972  United Kingdom .
1432378  4/1976  United Kingdom .
1463666  2/1977  United Kingdom .

OTHER PUBLICATIONS

Beattie et al., Chem. Abs. 86, 165063m, (1977).
Curran et al., Chem. Abs. 85, 46340u, (1976).
Gollan *Clinical Sci and Molec. Med.* 49, 237–245.
Beattie et al., J. Med. Chem. 20,714, (1977).

*Primary Examiner*—Mark L. Berch
*Attorney, Agent, or Firm*—Arthur E. Wilfond

[57] ABSTRACT

The invention relates to copper complexes of 5,6,7,8-tetrahydroquinoline-8-thiocarboxamides. The copper complexes are of value in the treatment of ulcers and hypersecretion in mammals.

14 Claims, No Drawings

COPPER COMPLEXES OF TETRAHYDROQUINOLINE DERIVATIVES HAVING ANTI-ULCER ACTIVITY

BACKGROUND OF THE INVENTION

United Kingdom Patent Specification 1432378 describes various thioamides which have anti-ulcer or anti-secretory activity. Included among the compounds disclosed in that specification are 5,6,7,8-tetrahydroquinoline-8-thiocarboxamides which may be substituted on the thioamide group by lower alkyl radicals. Both the unsubstituted and the substituted thioamides have anti-ulcer or anti-secretory activity. A further method of preparing these thioamides is described in United Kingdom Patent Specification 1463666.

I have now prepared copper complexes of some of the thioamides described in U.K. Specification No. 1432378 and have found that some possess anti-ulcer or anti-secretory activity whereas others do not. This invention is directed to the novel copper complexes possessing anti-ulcer or anti-secretory activity.

The invention provides a copper complex comprising copper (II) and a tetrahydroquinoline compound of formula I

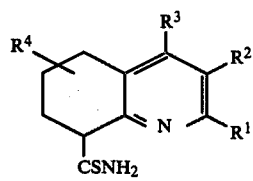

or a pharmaceutically acceptable acid addition salt thereof, wherein $R^1$, $R^2$, $R^3$ and $R^4$ are the same or different and represent hydrogen, alkyl of 1-6 carbon atoms, phenylloweralkyl or phenyl, and $R^4$ may also represent gem di-n-alkyl or $R^1$ and $R^2$ taken together represent an alkylene chain of 3 to 5 carbon atoms, which may be substituted by an $R^4$ radical, provided that when any two of $R^1$, $R^2$ and $R^3$ are alkyl groups present on adjacent carbon atoms they are selected from normal and secondary alkyl groups.

$R^4$ when a single radical may be in the same position as the thioamide group.

When any of $R^1$, $R^2$, $R^3$ and $R^4$ is an alkyl radical this is a lower alkyl radical which may be a straight or branched chain, having from 1 to 6 carbon atoms, e.g. methyl, ethyl, n-, and iso-propyl and n-, s- and t-butyl, $R^4$ may be a gemdimethyl group and when a single radical may be on the same carbon atom as the thioamide group. The term alkyl radical is also intended to embrace cyclic alkyl radicals e.g. cyclobutyl, cyclopentyl and cyclohexyl. When any of $R^1$, $R^2$, $R^3$ or $R^4$ is a phenylloweralkyl radical the lower alkyl portion may be as discussed above for a lower alkyl radical.

Particularly preferred compounds are those in which one or two of $R^1$, $R^2$, $R^3$ and $R^4$ are methyl and the others are hydrogen.

The copper complexes are prepared by treating a compound of formula I, or an acid addition salt thereof, preferably an aqueous solution, with a water-soluble copper (II) salt. The copper salt may be, for example, a copper halide e.g. copper (II) chloride, copper (II) bromide, copper (II) iodide or copper (II) fluoride, copper (II) sulphate or copper (II) nitrate.

If a salt of the compound of formula I is used this may be an addition salt with an inorganic acid, e.g. hydrochloric, hydrobromic, sulphuric or nitric acid or an organic acid e.g. fumaric, maleic or tartaric acid. Preferably the salt of compound I has the same anion as the copper salt.

The ratio of copper salt to compound I in the above reaction is preferably 1 gram atom of copper to 1 mol of compound I. However, more than 1 mol of compound I may be used e.g. 2 mols or up to 4 mols.

The following are specific examples of compounds of formula I which may be used in preparing the copper complexes of the invention.

2-phenyl-5,6,7,8-tetrahyroquinoline-8-thiocarboxamide;
5,6,7,8-tetrahydroquinoline-8-thiocarboxamide;
2-t-butyl-5,6,7,8-tetrahyroquinoline-8-thiocarboxamide;
2-methyl-5,6,7,8-tetrahydroquinoline-8-thiocarboxamide;
3-methyl-5,6,7,8-tetrahyroquinoline-8-thiocarboxamide;
sym-octahyroacridine-4-thiocarboxamide;
3,7,7-trimethyl-5,6,7,8-tetrahydroquinoline-8-thiocarboxamide;
4-methyl-5,6,7,8-tetrahydroquinoline-8-thiocarboxamide;
2,3,5,6,7,8-hexahydro-1H-cyclopenta[b]quinoline-5-thiocarboxamide;
2-ethyl-5,6,7,8-tetrahydroquinoline-8-thiocarboxamide;
2-n-butyl-5,6,7,8-tetrahydroquinoline-8-thiocarboxamide;
3,4-dimethyl-5,6,7,8-tetrahydroquinoline-8-thiocarboxamide;
3,5-dimethyl-5,6,7,8-tetrahydroquinoline-8-thiocarboxamide;
3,6-dimethyl-5,6,7,8-tetrahydroquinoline-8-thiocarboxamide;
2,4-dimethyl-5,6,7,8-tetrahydroquinoline-8-thiocarboxamide;
1,2,3,4,7,8,9,10-octahydro-6H-cyclohepta[b]quinoline-4-thiocarboxamide; and their acid addition salts especially the hydrohalide salts.

Some of the copper complexes of the invention when formed from a copper salt $CuX_2$ are believed to have the formula II

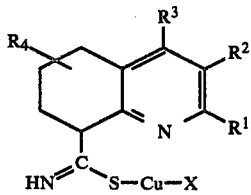

where $R^1$, $R^2$, $R^3$ and $R^4$ are as defined above and X is the atom derived from a monovalent anion of the copper salt used to prepare the complex. Compound II may be in the form of an acid addition salt e.g. with any acid HX. Compounds of this formula are included in the invention.

The starting compounds of formula I and their acid addition salts may be prepared as described in our U.K. Patent Specifications 1432378, or 1463666.

The copper complexes of the invention have been found to possess anti-ulcer activity as determined by the stress-induced erosion test of Senay & Levine, Proc. Soc. Exp. Biol. Med., 124, 1221-3(1967) and antisecretory activity by the test of H. Shay, D. Sun and H. Greenstein, Gastroenterology, 1954, 26, 903-13. The compounds which possess one or both these activities are considered to be anti-ulcer agents which can be used for the treatment of ulcers or hypersecretion in mammals.

Thus the copper complexes of the invention have anti-ulcer activity just as the parent compounds of formula I do. However we have prepared similar copper complexes from N-alkyl substituted thioamides of Specification 1432378 such as 3-methyl-5,6,7,8-tetrahydroquinoline-8-(N-methyl)thiocarboxamide and found that these do not possess significant activity in the anti-ulcer tests of Senay and Levine or Shay et al even though the parent compound of formula I has good activity in these tests.

The invention includes a pharmaceutical composition comprising an effective amount of a copper complex of the invention e.g. a compound of formula II, or an acid addition salt thereof, and a pharmaceutically acceptable carrier.

For the pharmaceutical carrier any suitable carrier known in the art can be used to prepare the pharmaceutical compositions. In such a composition, the carrier may be a solid, liquid, or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solution, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance, arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 25 mg to 500 mg or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminum hydroxide, magnesium hydroxide or bismuth carbonate, aluminum glycinate, calcium carbonate, magnesium trisilicate, sodium bicarbonate or the alumina gel described in British Specification No. 1,284,394.

The invention is illustrated by the following examples:

EXAMPLE 1

Copper complex of 3-methyl-5,6,7,8-tetrahydroquinoline-8-thiocarboxamide

3-Methyl-5,6,7,8-tetrahydroquinoline-8-thiocarboxamide hydrochloride (2.4 g) in water (15 ml) was treated at once with a solution of $CuCl_2.2H_2O$ (1.7 g) in water (15 ml). An instantaneous deep green colouration was followed by a milky precipitate which coagulated. On scratching deep yellow crystals were formed. These were removed by filtration, washed with water, ethanol and diethyl ether and dried to yield a copper complex (2.2 g) decomp >200° (Found: C, 39.9; H, 4.45; N, 8.4. $C_{22}H_{26}ClCu_2N_4OS_2.2HCl$ requires C, 39.8; H, 4.6; N, 8.4)

EXAMPLE 2

Copper complex of 3-methyl-5,6,7,8-tetrahydroquinoline-8-thiocarboxamide

A solution of 3-methyl-5,6,7,8-tetrahydroquinoline-8-thiocarboxamide (0.65 g) in water (10 ml) was treated with copper (II) chloride. $2H_2O$ (0.23 g) in water (5 ml). An instantaneous dark green colour was formed followed by a milky precipitate which was removed by repeated filtration. An orange precipitate formed which was allowed to crystallise giving the title compound (0.5 g) decomp >200°. (Found: C, 39.3; H, 4.4; N, 8.2. $C_{11}H_{12}ClCuN_2S$. HCl requires C, 38.8; H, 4.1; N, 8.2%)

The copper complex is believed to have the following structure:

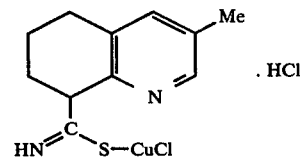

EXAMPLE 3

Copper complex of 3-methyl-5,6,7,8-tetrahydroquinoline-8-thiocarboxamide

A suspension of 3-methyl-5,6,7,8-tetrahydroquinoline-8-thiocarboxamide (2.06 g) in water (8 ml.) was treated with conc $HNO_3$ until it dissolved. A solution of Cu(NO$_3$)$_2$3H$_2$O (2.4 g) in water (4 ml.) was added. The solution turned dark green and was filtered and allowed to crystallise. The crystals were removed by filtration, washed with water and dried to give the title compound (2 g) mp >200° dec. (Found: C, 43.1; H, 4.8; N, 15.0; O, 15.1; S, 15.1; Cu, 6.8%). The analysis indicates the ratio of 3 moles of the tetrahydroquinoline to one gram atom of copper.

EXAMPLE 4

Copper complexes of tetrahydroquinoline-8-thiocarboxamides

Following the procedure of Example 1, but substituting for 3-methyl-5,6,7,8-tetrahydroquinoline-8-thiocarboxamide an equivalent amount of the following compounds copper complexes are obtained:

2-phenyl-5,6,7,8-tetrahydroquinoline-8-thiocarboxamide;

5,6,7,8-tetrahydroquinoline-8-thiocarboxamide;

2-methyl-5,6,7,8-tetrahydroquinoline-8-thiocarboxamide; sym-octahydroacridine-4-thiocarboxamide;

4-methyl-5,6,7,8-tetrahydroquinoline-8-thiocarboxamide 2-n-butyl-5,6,7,8-tetrahydroquinoline-8-thiocarboxamide 3,5-dimethyl-5,6,7,8-tetrahydroquinoline-8-thiocarboxamide.

| Test | mpk | Inhib | | |
|---|---|---|---|---|
| Stress-induced erosion (Senay & Levine) | p.o. 100 | 91% | | |
| | 30 | 92% | | |
| | 10 | 42. N.S. | | |
| | Dose | % decrease in | | |
| Anti-secretory (Shay et al) | mg/kg (i-duod) | Vol. | Conc. | Free acid | Total acid |
| | 30 | 54% | 28% N.S. | 60%* | 49%* |
| | 10 | 16% N.S. | 30%* | 41%* | 35%* |

N.S. = Not significant

The invention includes a method of treating ulcers or hypersecretion in an afflicted mammal which method comprises administering to said mammal an effective amount of a copper complex with a thioamide of formula I or an acid addition salt thereof as described herein, e.g. a compound of formula II.

The amount of copper complex used will depend on the compound employed, the severity and nature of the ulceration or hypersecretion and the mammal being treated. With large mammals (about 70 kg body weight) by the oral route the dose is from about 25 to about 500 mg every four hours or as needed.

I claim:

1. A crystalline copper complex consisting essentially of copper (II), a pharmaceutically acceptable anion of water-soluble copper (II) salt and a tetrahydroquinoline compound of formula I

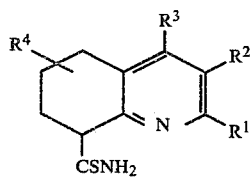

or a pharmaceutically acceptable acid addition salt thereof, wherein R$^1$, R$^2$, R$^3$, and R$^4$ are the same or different and represent hydrogen, alkyl of 1-6 carbon atoms, phenylloweralkyl or phenyl, and R$^4$ may also represent gem di-methyl or R$^1$ and R$^2$ taken together represent an alkylene chain of 3 to 5 carbon atoms, which may be substituted by an R$^4$ radical, provided that when any two of R$^1$, R$^2$, and R$^3$ are alkyl groups present on adjacent carbon atoms they are selected from normal and secondary alkyl groups.

2. A copper complex as claimed in claim 1, wherein the tetrahydroquinoline compound of formula I is one in which R$^1$, R$^2$, R$^3$ and R$^4$ are selected from hydrogen and alkyl of 1-4 carbon atoms.

3. A copper complex as claimed in claim 1, wherein the tetrahydroquinoline compound of formula I is one in which R$^1$, R$^2$, R$^3$ and R$^4$ are selected from hydrogen and methyl.

4. A copper complex as claimed in claim 1 wherein the tetrahydroquinoline compound is selected from 3-methyl-5,6,7,8-tetrahydroquinoline-8-thiocarboxamide and pharmaceutically acceptable acid addition salts thereof.

5. A crystalline compound of the formula

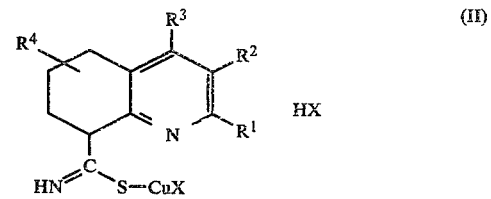

wherein X is a pharmaceutically acceptable monovalent anion of a water-soluble copper (II) salt and R$^1$, R$^2$, R$^3$, and R$^4$, are as defined in claim 1.

6. A compound as claimed in claim 5, wherein X is halogen and R$^1$, R$^2$, R$^3$ and R$^4$ are selected from hydrogen and methyl.

7. A compound of the formula

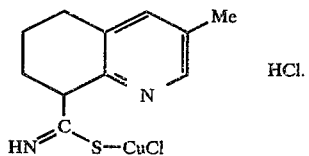

8. A pharmaceutical composition for use in treatment of ulcers or hypersecretion comprising an effective amount of a copper complex as claimed in claim 1 and a pharmaceutical carrier.

9. A pharmaceutical composition as claimed in claim 8, in unit dosage form.

10. A pharmaceutical composition for use in treatment of ulcers or hypersecretion comprising an effective amount of a compound of formula II as claimed in claim 5 and a pharmaceutical carrier.

11. A pharmaceutical composition as claimed in claim 10 in unit dosage form.

12. A method of treating ulcers or hypersecretion in an afflicted mammal which method comprises administering to said mammal an effective amount of the pharmaceutical composition of claim 8.

13. A method of treating ulcers or hypersecretion in an afflicted mammal which method comprises administering to said mammal an effective amount of the pharmaceutical composition of claim 10.

14. A copper complex formed by reacting a compound of formula I, as defined in claim 1 or an acid addition salt thereof, with a water-soluble copper (II) salt in the ratio of 1 gram atom of copper to from 1 to 4 moles of the compound of formula I.

* * * * *